United States Patent
Kollgaard et al.

(10) Patent No.: US 8,286,487 B2
(45) Date of Patent: Oct. 16, 2012

(54) ULTRASONIC APERTURE SCANNING SYSTEM AND METHOD

(75) Inventors: Jeffrey R. Kollgaard, Kent, WA (US); Barry A. Fetzer, Renton, WA (US); Kevin M. Uhl, Snohomish, WA (US)

(73) Assignee: The Boeing Company, Chicago, IL (US)

( * ) Notice: Subject to any disclaimer, the term of this patent is extended or adjusted under 35 U.S.C. 154(b) by 468 days.

(21) Appl. No.: 12/363,742

(22) Filed: Jan. 31, 2009

(65) Prior Publication Data
US 2010/0198076 A1    Aug. 5, 2010

(51) Int. Cl.
*G01N 29/07*    (2006.01)
(52) U.S. Cl. ............................................. 73/598; 73/600
(58) Field of Classification Search ..................... 73/588, 73/598, 600
See application file for complete search history.

(56) References Cited

U.S. PATENT DOCUMENTS

| 4,322,975 A * | 4/1982 | Schmidt et al. .................. 73/633 |
| 7,222,514 B2 | 5/2007 | Kollgaard et al. |
| 2007/0084290 A1 * | 4/2007 | Fetzer et al. .................... 73/627 |

* cited by examiner

*Primary Examiner* — Hezron E Williams
*Assistant Examiner* — Paul West
(74) *Attorney, Agent, or Firm* — Parsons Behle & Latimer

(57) ABSTRACT

An ultrasonic aperture scanning system includes a transducer insert having an insert plug, an ultrasonic transducer carried by the transducer insert and an indicator unit having at least one indicator interfacing with the ultrasonic transducer.

22 Claims, 6 Drawing Sheets

ULTRASONIC APERTURE SCANNING SYSTEM AND METHOD

TECHNICAL FIELD

The present disclosure relates to apparatus for scanning materials to detect delamination of the materials. More particularly, the present disclosure relates to an ultrasonic aperture scanning system and method which may be effective in detecting delamination caused by the drilling of apertures in or the removal of fasteners from composite materials.

BACKGROUND

With the advent of composite structures has come the drilling of apertures in and the removal of fasteners from composite laminates as a frequent production and maintenance operation. Drilling and fastener removal, however, may cause delamination of the laminates.

A method to detect delamination of composite laminates may involve the performance of ultrasonic checks around the aperture which is drilled or from which a fastener is removed. This may be accomplished by manually passing a transducer around the aperture or using a circle template to scan the transducer around the aperture. Interpretation may be made using an A-scan oscilloscope trace. However, this technique may require that operations stop while the scan is made. Moreover, the A-scan results may require interpretation by a certified operator.

Therefore, an ultrasonic aperture scanning system and method are needed which indicate whether or not delamination exists in a composite laminate adjacent to an aperture and which can be operated or implemented by an unskilled operator.

SUMMARY

The present disclosure is generally directed to an ultrasonic aperture scanning system. An illustrative embodiment of the ultrasonic aperture scanning system 1 includes a transducer insert 2 having an insert plug 4, an ultrasonic transducer 10 carried by the transducer insert 2 and an indicator unit 14 having at least one indicator 17, interfacing with the ultrasonic transducer 10.

Another illustrative embodiment of the ultrasonic aperture scanning system 1 may include a transducer insert having a generally elongated index portion 3, an insert plug 4 extending from the index portion 3, an ultrasonic transducer 10 carried by the index portion 3 of the transducer insert 2 and an indicator unit 14 having a damage indicator 17 and a no damage indicator 19 interfacing with the ultrasonic transducer 10.

The present disclosure is further generally directed to an ultrasonic aperture scanning method. An illustrative embodiment of the method 800 may include providing a structure having first and second surfaces and an aperture extending between the first and second surfaces 802, providing a transducer insert with an insert plug and an ultrasonic transducer 804, extending the insert plug of the transducer insert into the aperture 806, emitting a first ultrasonic pulse from the ultrasonic transducer into the structure adjacent to the aperture 808, detecting a first ultrasonic echo profile from the structure 810, conducting a circumferential scan into the structure around the aperture by emitting a second ultrasonic pulse from the ultrasonic transducer into the structure circumferentially around the aperture and detecting a second ultrasonic echo profile from the structure 814; and providing an indication if the second echo profile deviates from the first echo profile 816.

Another illustrative embodiment of the ultrasonic aperture scanning system 1 may include a transducer insert 2 comprising a generally elongated index portion 3; an insert plug 4 extending from the index portion 3 in generally perpendicular relationship with respect to the index portion 3; a transducer opening 7 provided in the index portion 3 generally adjacent to the insert plug 4; and an ultrasonic transducer 10 seated in the transducer opening 7 and an indicator unit 14 comprising an indicator unit housing 15; a processor 16 provided in the indicator unit housing 15; a generally elongated, flexible connecting cable 22 connecting the processor 16 and the ultrasonic transducer 10; a damage indicator comprising a red light 16 carried by the indicator unit housing 15 and interfacing with the processor 16; and a no damage indicator comprising a green light 19 carried by the indicator unit housing 15 and interfacing with the processor 16.

Another illustrative embodiment of the ultrasonic aperture scanning method 900 may include providing a structure having first and second surfaces and an aperture extending between the first and second surfaces 902; providing a transducer insert having an index portion, an insert plug extending from the index portion, a transducer opening provided in the index portion generally adjacent to the insert plug and an ultrasonic transducer seated in the transducer opening 904; extending the insert plug of the transducer insert into the aperture 906; emitting a first ultrasonic pulse from the ultrasonic transducer into the structure at a reference point adjacent to the aperture 908; detecting a first ultrasonic echo profile reflected from the structure 910; memorizing the first ultrasonic echo profile as a reference signal 912; conducting a circumferential scan into the structure around the aperture by emitting a second ultrasonic pulse from the ultrasonic transducer into the structure circumferentially around the aperture and detecting a second ultrasonic echo profile reflected from the structure 914; illuminating a red light if the second echo profile deviates from the first echo profile 918; and illuminating a green light if the second echo profile does not deviate from the first echo profile 920.

BRIEF DESCRIPTION OF THE ILLUSTRATIONS

DETAILED DESCRIPTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the invention and are not intended to limit the scope of the invention, which is defined by the claims. Furthermore, there is no intention to be bound by any expressed or implied theory presented in the preceding technical field, background, brief summary or the following detailed description.

Figure 1:
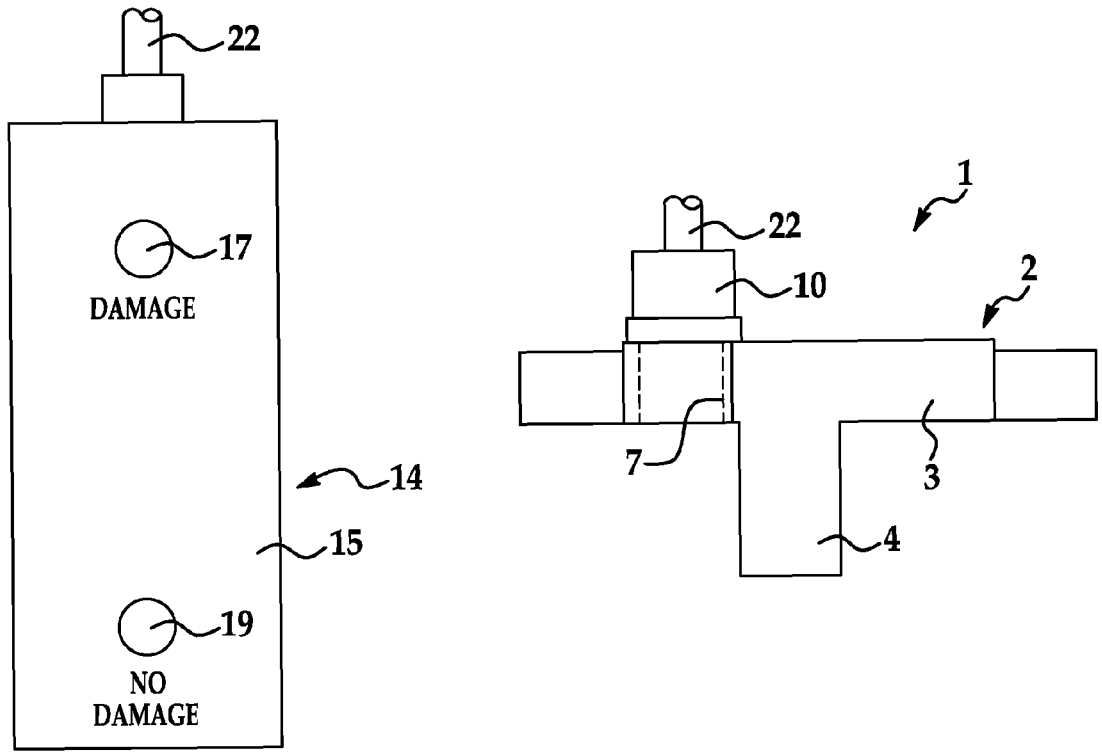
FIG. 1 is a front view, partially in section, of an illustrative embodiment of the ultrasonic aperture scanning system.
Figure 2:
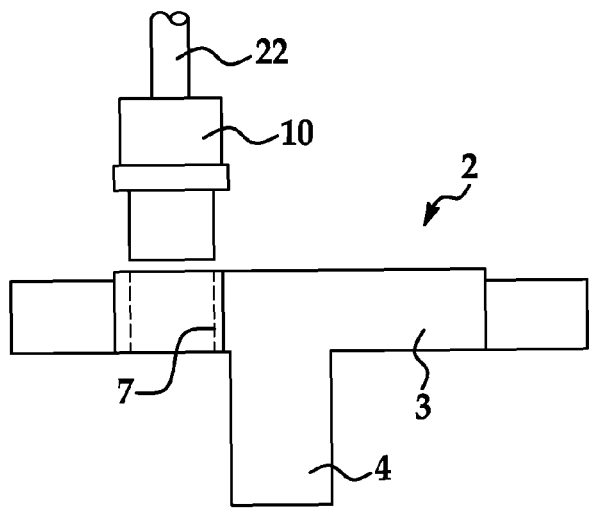
FIG. 2 is a front view of a transducer insert of an illustrative embodiment of the ultrasonic aperture scanning system, with a transducer removed from the transducer insert.
Figure 3:
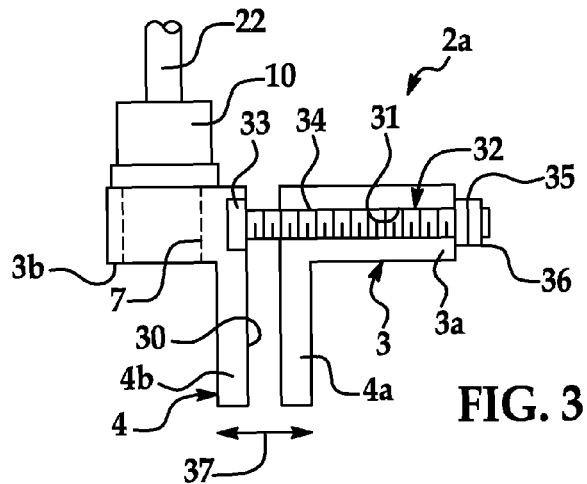
FIG. 3 is a front view of a transducer insert assembly of an alternative illustrative embodiment of the ultrasonic aperture scanning system.
Figure 4:
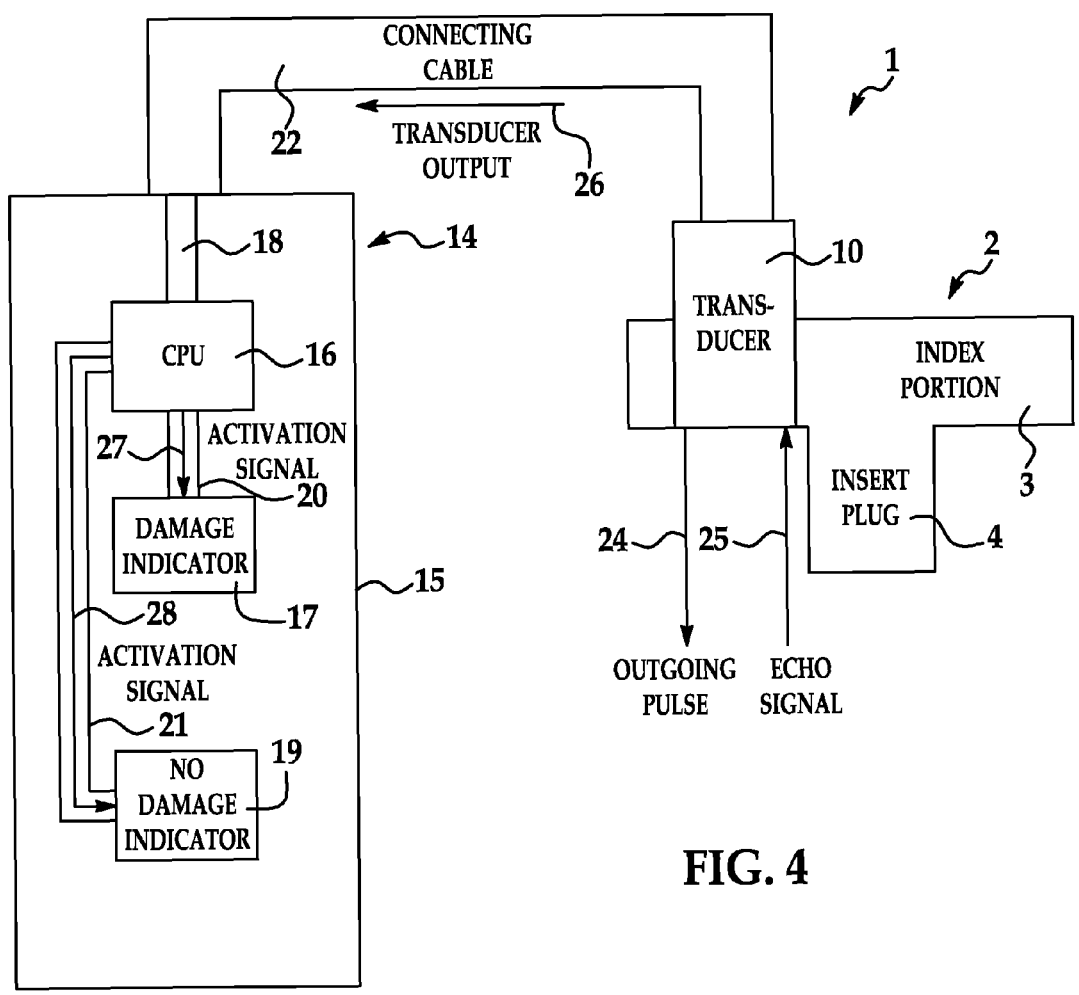
FIG. 4 is a schematic block diagram of an illustrative embodiment of the ultrasonic aperture scanning system.

Referring initially to FIGS. 1-4, an illustrative embodiment of the ultrasonic aperture scanning system, hereinafter system, is generally indicated by reference numeral 1 in FIGS. 1 and 4. The system 1 may include a transducer insert 2 which may include a generally elongated index portion 3 and an insert plug 4 which extends from the index portion 3. The insert plug 4 may be disposed at a generally 90-degree angle with respect to the index portion 3.

As shown in FIGS. 1 and 2, in some embodiments the insert plug 4 of multiple transducer inserts 2 may be fabricated in various diameters depending on the application of the system 1, which will be hereinafter described. Therefore, the transducer inserts 2 with insert plugs 4 of various diameters may be interchangeable in the system 1 depending on the application of the system 1. As shown in FIG. 3, in other embodiments, the system 1 may include a transducer insert 2a the index portion 3 of which may include a first index portion segment 3a and a second index portion segment 3b from which respective insert plug sections 4a and 4b, respectively, of the insert plug 4 extends. The insert plug sections 4a, 4b may be divided by a plug space 30. An index pin opening 31 may extend through the first segment 3a and a portion of the second segment 3b. An adjustable index pin 32 may include a pin head 33 which is seated in the second segment 3b of the index portion 3 and a threaded pin shaft 34 which extends from the pin head 33, spans the plug space 30 and threadably engages the index pin opening 31. A lock washer and a nut 36 may be provided on the extending end of the pin shaft 34. Accordingly, depending on the application of the system 1, the width or diameter of the insert plug 4 can be selectively varied, as indicated by the arrow 37, by threading or unthreading the nut 36 on the pin shaft 34 of the adjustable index pin 32.

A transducer opening 7 may extend through the index portion 3 on one side of the insert plug 4. An ultrasonic transducer 10 may be inserted in the insert plug 4. An indicator unit 14 may be connected to the ultrasonic transducer 10 such as through a connecting cable 22. As shown in FIG. 4, the indicator unit 14 may include an indicator unit housing 15 which contains the components of the indicator unit 14. A CPU 16 may be provided in the indicator unit housing 15 and connected to the connecting cable 22 through a connection 18. A damage indicator 17 may be connected to the CPU 16 through a connection 20. A no damage indicator 19 may be connected to the CPU 16 through a connection 21. As shown in FIG. 1, the damage indicator 17 and the no damage indicator 19 may be provided on the exterior of the indicator housing 15. The damage indicator 17 and the no damage indicator 19 may be visually distinguishable from each other. In some embodiments, the damage indicator 17 may be a red light and the no damage indicator 19 may be a green light, for example and without limitation.

Referring next to FIGS. 2 and 4-6, in typical application the system 1 may be used to determine the presence or absence of delamination 45 (FIG. 6) in or adjacent to an aperture 44 in a laminated composite structure 40. The laminated composite structure 40 may have multiple stacked plies or laminates 41. The aperture 44 may extend through the plies or laminates 41 from a first surface 42 to a second surface 43 of the laminated composite structure 40. Prior to testing for the presence of delamination 45 using the system 1, the aperture 44 may have been drilled in the laminated composite structure 40 preparatory to insertion of a fastener (not shown) through the aperture 44. Alternatively, a fastener (not shown) may have been removed from the aperture 44 prior to testing.

Figure 5:
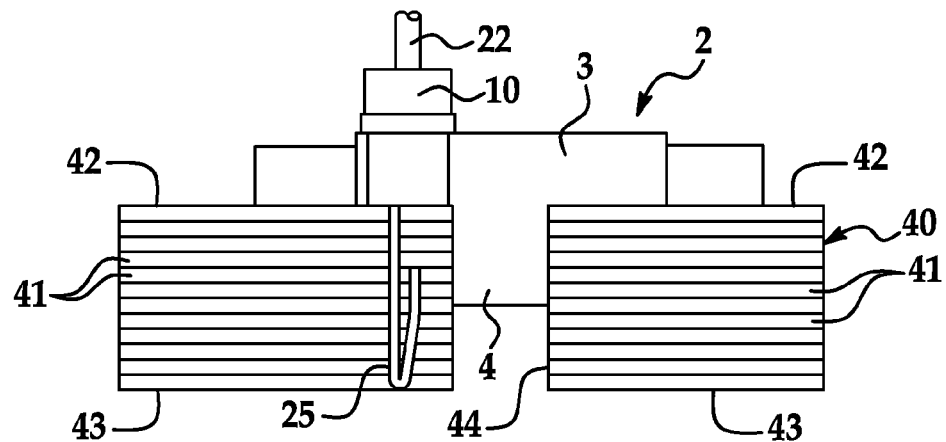
FIG. 5 is a sectional view of a laminated composite structure with an insert plug of the transducer insert inserted in an aperture in the structure, a transducer placed at a first surface of the structure adjacent to the aperture and an ultrasonic echo signal reflected off a second surface of the structure, indicating lack of delamination in the structure.
Figure 6:
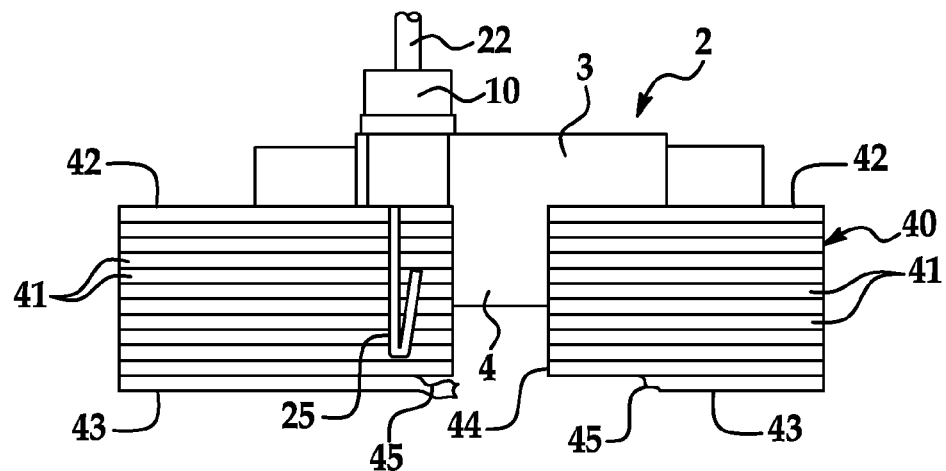
FIG. 6 is a sectional view of a laminated composite structure with the insert plug inserted in an aperture in the structure and an ultrasonic echo signal reflected from between the first and second surfaces of the structure, indicating delamination in the structure.

As shown in FIG. 2, the ultrasonic transducer 10, connected to the indicator unit 14 (FIG. 4) via the connecting cable 22, may be inserted in the transducer opening 7 provided in the index portion 3 of the transducer insert 2. As shown in FIGS. 5 and 6, the insert plug 4 of the transducer insert 2 may be inserted into the aperture 44 in the laminated composite structure 40. In the embodiment shown in FIG. 2, the transducer insert 2 having an insert plug 4 the diameter or width of which matches the diameter or width of the aperture 44 in the laminated composite structure 40 may be selected. In the embodiment shown in FIG. 3, the diameter or width of the insert plug 4 may be selected to match the diameter or width of the aperture 44 by rotation of the adjustable index pin 32 in the index pin opening 31. The insert plug 4 may hold the transducer 10 at the correct radius from the center of the aperture 44 to enable a circumferential scan of the laminated composite structure 40, as will be hereinafter described.

A reference scan of the structure 40 may initially be made at any point adjacent to the aperture 44 in order to obtain a memorized reference signal. As shown in FIG. 4, the ultrasonic transducer 10 may be operated to emit an ultrasonic outgoing pulse 24 into the laminated composite structure 40 adjacent to the aperture 44. As shown in FIG. 5, in the event that none of the plies or laminates 41 in the laminated composite structure 40 is delaminated, an echo signal 25 which indicates the undamaged profile of the plies or laminates 41 at the scanned location may be reflected from the second surface 43 of the structure 40 and back to the ultrasonic transducer 10. The ultrasonic transducer 10 may then transmit a transducer output signal 26 which indicates the undamaged state of the structure 40 through the connecting cable 22 to the CPU 18 of the indicator unit 14. The CPU 18 may then interpret the transducer output signal 26 as a no damage signal (indicating the absence of delamination in the structure 40), memorize the transducer output signal 26 and activate the no damage indicator 19 through an activation signal 28. The no damage indicator 19 may provide a visual indication (such as green light) to the operator of the system 1 which indicates that no delamination was detected in the scanned area of the structure 40 which surrounds the aperture 44.

After the reference scan is taken at the selected location adjacent to the aperture 44, a circumferential scan of the area which surrounds the aperture 44 may then be taken to determine the presence of delamination 45 in the structure 40 at any location adjacent to the aperture 44. In the event that no delamination 45 is detected in the structure 40 during the circumferential scan, a constant echo signal 25 may be reflected back to the ultrasonic transducer 10 and the CPU 16 may activate the no damage indicator 19. As shown in FIG. 6, in the event that the circumferential scan of the area around the aperture 44 indicates that a delamination 45 exists within the structure 40, an echo signal 25 which indicates the delaminated profile of the plies or laminates 41 at the scanned location may be reflected from between the first surface 42 an the second surface 43 of the structure 40 and back to the ultrasonic transducer 10. The ultrasonic transducer 10 may then transmit a transducer output signal 26 (FIG. 4) which indicates the delaminated state of the structure 40 through the connecting cable 22 to the CPU 18 of the indicator unit 14. The CPU 18 may then compare that transducer output signal 26 to the memorized reference transducer output signal 26 previously received during the reference scan. In the event that the transducer output signal 28 obtained at any point during the circumferential scan deviates from the memorized reference transducer output signal 28 received during the reference scan, the CPU 18 may interpret the transducer output signal 26 as a damage signal (indicating the presence of the delamination 45 in the structure 40) and accordingly, activate the damage indicator 17 through an activation signal 27. The damage indicator 17 may provide a visual indication (such as red light) to the operator of the system 1 which indicates that the delamination 45 was detected in the scanned area of the structure 40 which surrounds the aperture 44. Corrective measures may then be taken to repair the laminated composite structure 40.

Figure 7:
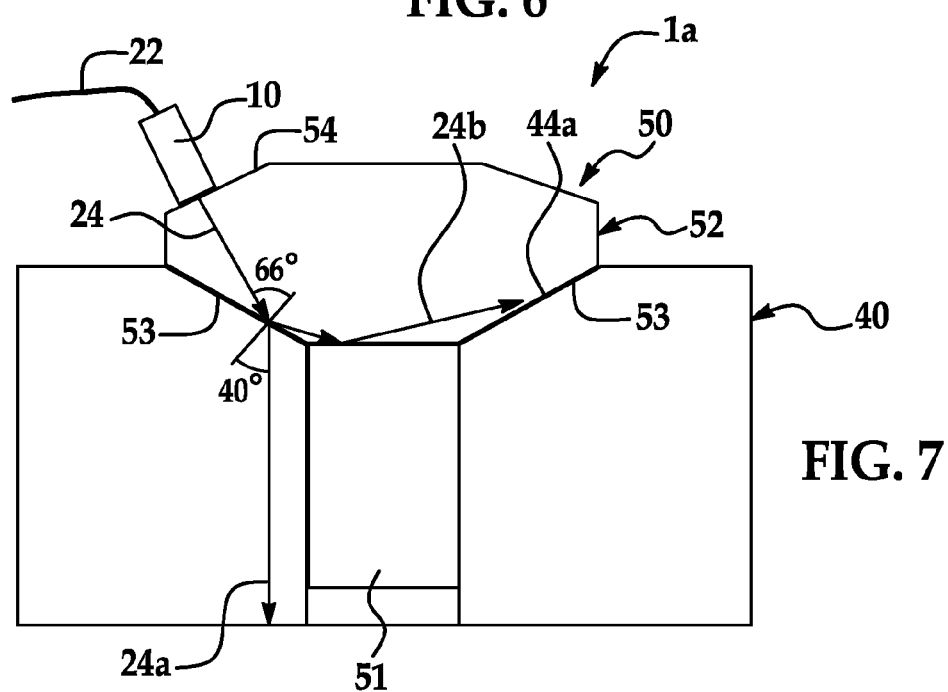
FIG. 7 is a sectional view of a laminated composite structure having a countersunk aperture, with a beam-steering insert plug having an acoustically-matched material inserted in the aperture to direct an ultrasonic pulse through the structure and adjacent to the aperture.

Referring next to FIG. 7, implementation of an alternative illustrative embodiment of the system 1a is shown in the scanning of a laminated composite structure 40 having a countersunk aperture 44a. A beam-steering transducer insert 50 of the system 1a may include an insert plug 51 which is inserted in the countersunk aperture 44a. An index portion 52 may be provided on the insert plug 51. The index portion 52 may have a beveled engaging surface 53 which may be configured to seat against the countersunk opening of the countersunk aperture 44a. A beveled transducer surface 54, against which the ultrasonic transducer 10 is placed, may be provided in the index portion 52 generally opposite the beveled engaging surface 53. The beam-steering transducer insert 50 may be an acoustically-matched material to direct the outgoing ultrasonic pulse 24 from the ultrasonic transducer 10 into a directed beam 24a which is directed through the laminated composite structure 40 adjacent to the countersunk aperture 44a. Snells' Law suggests that brass, with an ultrasonic velocity of V=4280 m/sec, may create the desired beam bending in the 100 degree countersinks used with CFRP fasteners. A deflected beam 24b may split from the outgoing pulse 24 through the index portion 52.

Figure 8:
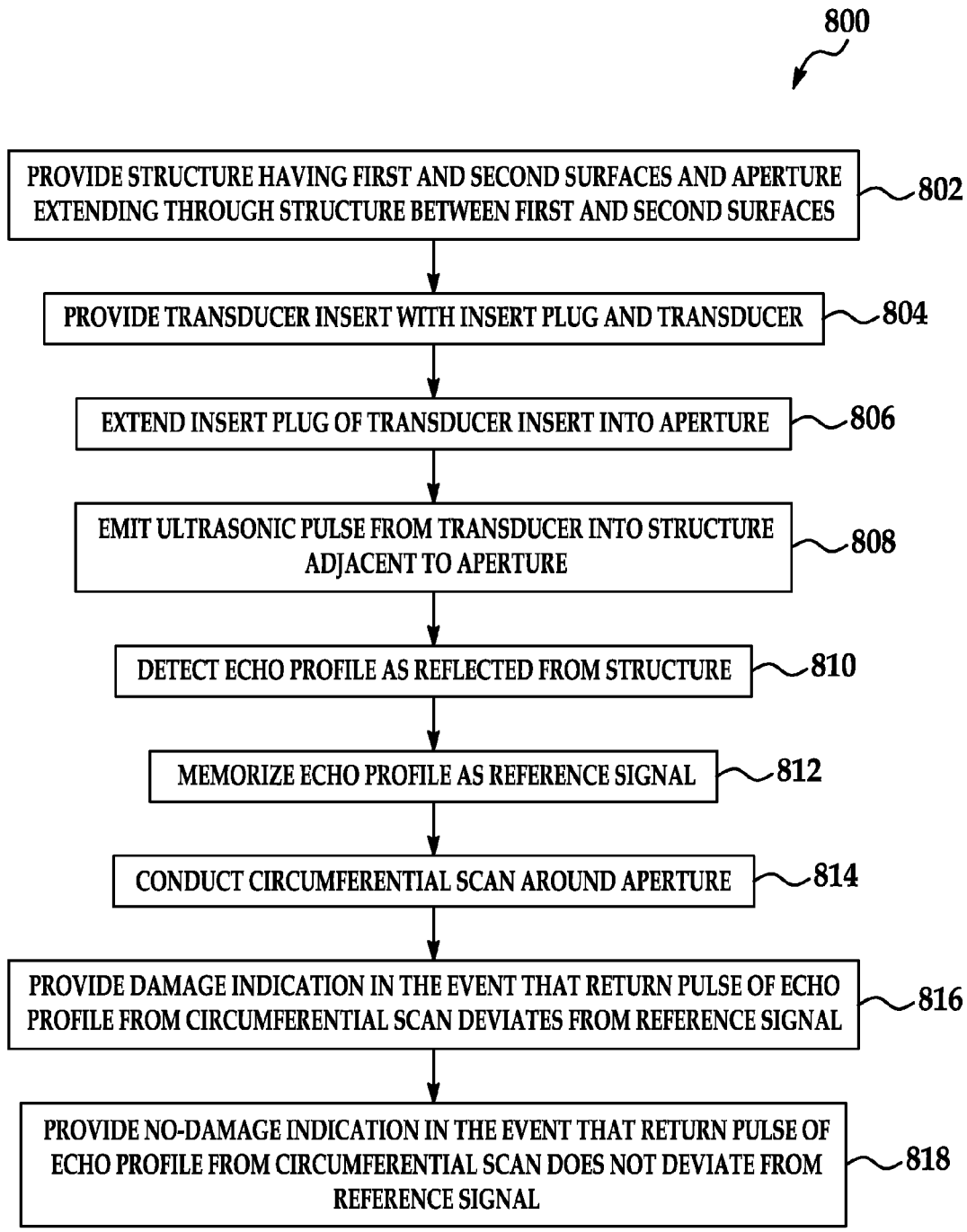
FIG. 8 is a flow diagram which illustrates an illustrative embodiment of an ultrasonic aperture scanning method.

Referring next to FIG. 8, a flow diagram 800 which illustrates an illustrative embodiment of an ultrasonic aperture scanning method is shown. In block 802, a structure having first and second surfaces and an aperture extending through the structure between the first and second surfaces is provided. In block 804, a transducer insert with an insert plug and an ultrasonic transducer is provided. In block 806, the insert plug of the transducer insert is extended into the aperture. In block 808, an ultrasonic pulse is emitted from the transducer into the structure adjacent to the aperture. In block 810, an ultrasonic echo profile reflected from the structure is detected. In block 812, the echo profile received in block 810 is memorized as a reference signal. In block 814, a circumferential scan around the aperture is conducted. In block 816, a damage indication is provided in the event that a return pulse of the echo profile from the circumferential scan deviates from the reference signal. In block 818, a no damage indication may be provided in the event that the return pulse of the echo profile from the circumferential scan does not deviate from the reference signal.

Figure 9:
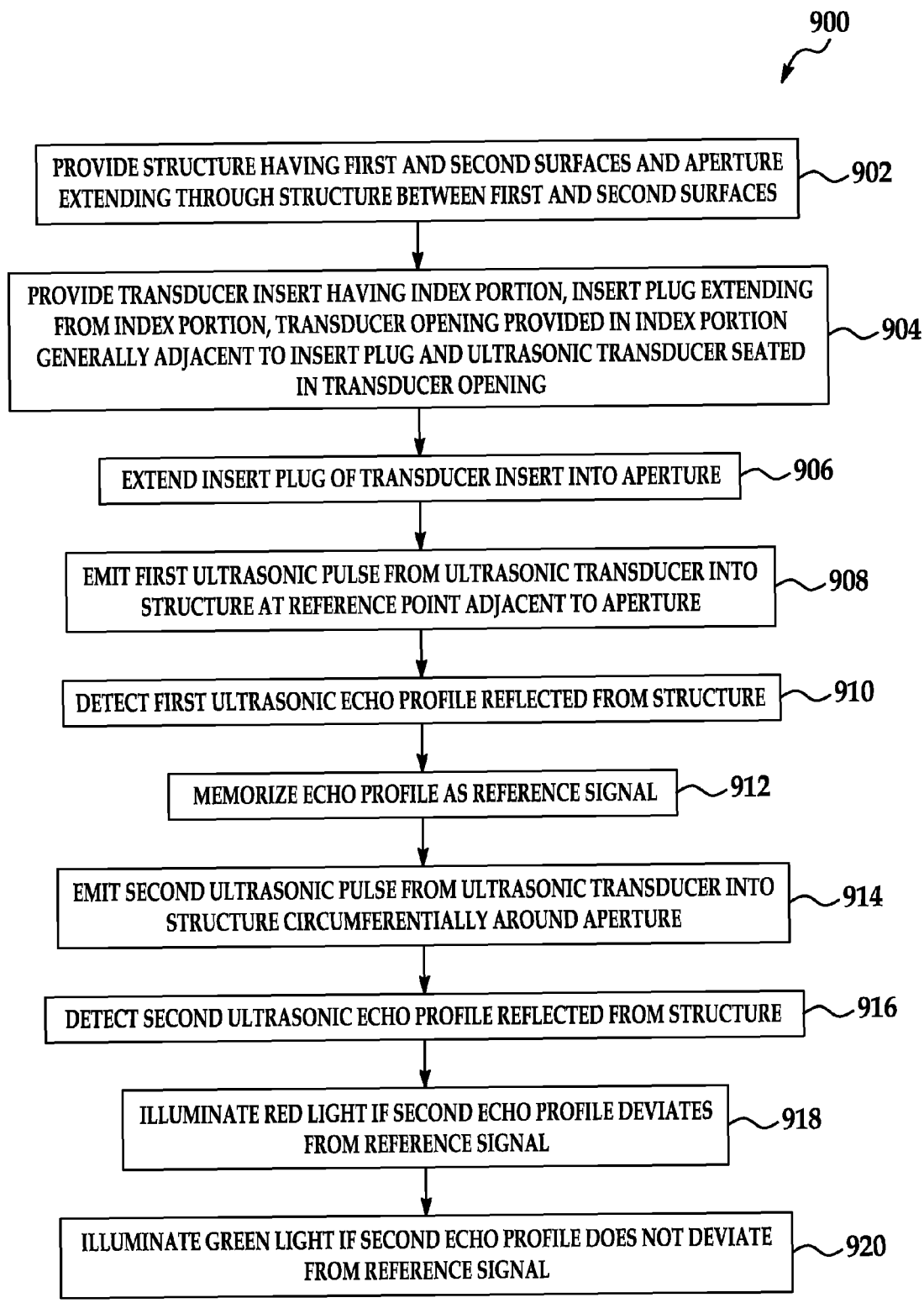
FIG. 9 is a flow diagram which illustrates an alternative illustrative embodiment of an ultrasonic aperture scanning method.

Referring next to FIG. 9, a flow diagram 900 which illustrates an illustrative ultrasonic aperture scanning method is shown. In block 902, a structure having first and second surfaces and an aperture extending between the first and second surfaces is provided. In block 904, a transducer insert having an index portion, an insert plug extending from the index portion, a transducer opening provided in the index portion generally adjacent to the insert plug and an ultrasonic transducer seated in the transducer opening is provided. In block 906, the insert plug of the transducer insert is extended into the aperture. In block 908, a first ultrasonic pulse is emitted from the ultrasonic transducer into the structure at a reference point adjacent to the aperture. In block 910, a first ultrasonic echo profile is reflected from the structure. In block 912, the first echo profile obtained in block 910 is memorized as a reference signal. In block 914, a second ultrasonic pulse is emitted from the ultrasonic transducer into the structure circumferentially around the aperture. In block 916, a second ultrasonic echo profile is reflected from the structure throughout the circumferential scan. In block 918, the red light is illuminated if the second echo profile deviates from the reference signal at any point during the circumferential scan. In block 920, the green light is illuminated if the second echo profile does not deviate from the reference signal throughout the reference scan.

Figure 10:
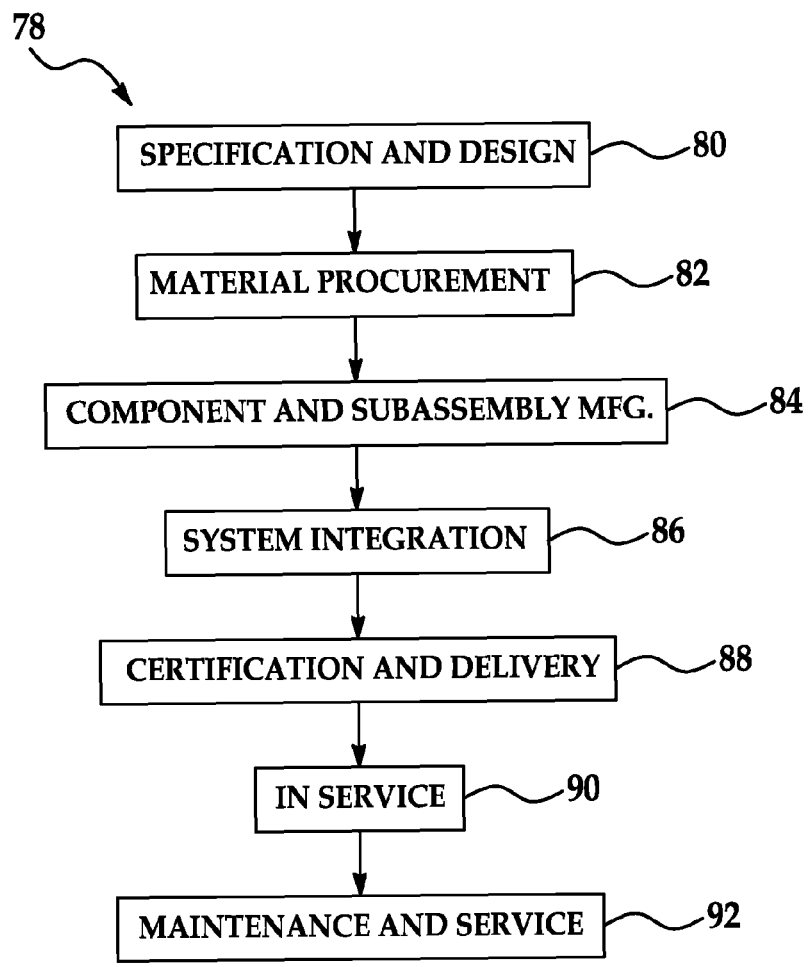
FIG. 10 is a flow diagram of an aircraft production and service methodology.
Figure 11:
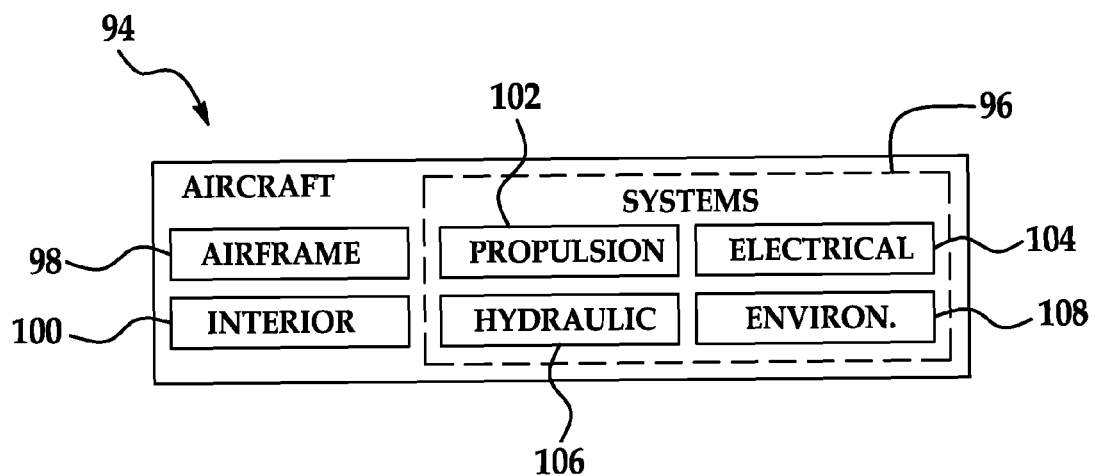
FIG. 11 is a block diagram of an aircraft.

Referring next to FIGS. 10 and 11, embodiments of the disclosure may be used in the context of an aircraft manufacturing and service method 78 as shown in FIG. 10 and an aircraft 94 as shown in FIG. 11. During pre-production, exemplary method 78 may include specification and design 80 of the aircraft 94 and material procurement 82. During production, component and subassembly manufacturing 84 and system integration 86 of the aircraft 94 takes place. Thereafter, the aircraft 94 may go through certification and delivery 88 in order to be placed in service 90. While in service by a customer, the aircraft 94 may be scheduled for routine maintenance and service 92 (which may also include modification, reconfiguration, refurbishment, and so on).

Each of the processes of method 78 may be performed or carried out by a system integrator, a third party, and/or an operator (e.g., a customer). For the purposes of this description, a system integrator may include without limitation any number of aircraft manufacturers and major-system subcontractors; a third party may include without limitation any number of vendors, subcontractors, and suppliers; and an operator may be an airline, leasing company, military entity, service organization, and so on.

As shown in FIG. 11, the aircraft 94 produced by exemplary method 78 may include an airframe 98 with a plurality of systems 96 and an interior 100. Examples of high-level systems 96 include one or more of a propulsion system 102, an electrical system 104, a hydraulic system 106, and an environmental system 108. Any number of other systems may be included. Although an aerospace example is shown, the principles of the invention may be applied to other industries, such as the automotive industry.

The apparatus embodied herein may be employed during any one or more of the stages of the production and service method 78. For example, components or subassemblies corresponding to production process 84 may be fabricated or manufactured in a manner similar to components or subassemblies produced while the aircraft 94 is in service. Also one or more apparatus embodiments may be utilized during the production stages 84 and 86, for example, by substantially expediting assembly of or reducing the cost of an aircraft 94. Similarly, one or more apparatus embodiments may be utilized while the aircraft 94 is in service, for example and without limitation, to maintenance and service 92.

Although the embodiments of this disclosure have been described with respect to certain exemplary embodiments, it is to be understood that the specific embodiments are for purposes of illustration and not limitation, as other variations will occur to those of skill in the art.

What is claimed is:

1. An ultrasonic aperture scanning system, comprising:
    a transducer insert having an insert plug, the insert plug having a first plug section and a second plug section divided by a selectively varied plug space;
    an ultrasonic transducer carried by said transducer insert and adapted to transmit an outgoing pulse and receive an echo signal along a path immediately adjacent and parallel to said insert plug; and
    an indicator unit having at least one indicator interfacing with said ultrasonic transducer.

2. The system of claim 1 wherein said transducer insert comprises a generally elongated index portion and wherein said insert plug extends from said index portion.

3. The system of claim 2 where said insert plug is disposed in a generally perpendicular relationship with respect to said index portion.

4. The system of claim 2 further comprising a transducer opening provided in said index portion generally adjacent to said insert plug and wherein said ultrasonic transducer is seated in said transducer opening.

5. The system of claim 1 further comprising a generally elongated, flexible connecting cable connecting said indicator unit and said ultrasonic transducer.

6. The system of claim 1 wherein said transducer insert comprises first and second index portion segments and the first plug section and the second plug section extend from said first and second index portion segments, respectively, and further comprising an adjustable index pin threadably engaging said first and second index portion segments, respectively, wherein rotation of the index pin increases or decreases the plug space between the first plug section and the second plug section.

7. The system of claim 1 wherein said transducer insert comprises a generally elongated index portion and wherein said insert plug extends from said index portion, and further comprises a beveled engaging surface and a beveled transducer surface provided in said index portion, wherein an end of the ultrasonic transducer is against the beveled transducer surface.

8. The system of claim 7 wherein said transducer insert comprises brass.

9. An ultrasonic aperture scanning system, comprising:
    a transducer insert having a generally elongated index portion and an insert plug extending from said index portion, the insert plug having a first plug section and a second plug section divided by a selectively varied plug space;
    an ultrasonic transducer carried by said index portion of said transducer insert and adapted to transmit an outgoing pulse and receive an echo signal along a path immediately adjacent and parallel to said insert plug; and
    an indicator unit having a damage indicator and a no damage indicator interfacing with said ultrasonic transducer.

10. The system of claim 9 wherein said insert plug is disposed in a generally perpendicular relationship with respect to said index portion.

11. The system of claim 9 further comprising a transducer opening provided in said index portion generally adjacent to said insert plug and wherein said ultrasonic transducer is seated in said transducer opening.

12. The system of claim 9 further comprising a generally elongated, flexible connecting cable connecting said indicator unit and said ultrasonic transducer.

13. The system of claim 9 wherein said transducer insert comprises first and second index portion segments and the first plug section and the second plug section extend from said first and second index portion segments, respectively, and further comprising an adjustable index pin threadably engaging said first and second index portion segments, respectively, wherein rotation of the index pin increases or decreases the plug space between the first plug section and the second plug section.

14. The system of claim 9 further comprising a beveled engaging surface provided in said index portion and a beveled transducer surface provided in said index portion generally opposite said beveled engaging surface, wherein an end of the ultrasonic transducer is against the beveled transducer surface.

15. The system of claim 14 wherein said transducer insert comprises brass.

16. An ultrasonic aperture scanning method, comprising:
    providing a structure having first and second surfaces and an aperture extending between said first and second surfaces;
    providing a transducer insert with an insert plug and an ultrasonic transducer and adapted to transmit an outgoing pulse and receive an echo signal along a path immediately adjacent and parallel to said insert plug, the insert plug having a first plug section and a second plug section divided by a selectively varied plug space;
    extending said insert plug of said transducer insert into said aperture;
    emitting a first ultrasonic pulse from said ultrasonic transducer into said structure adjacent to said aperture;
    detecting a first ultrasonic echo profile as a reference signal from said structure;
    conducting a circumferential scan into said structure around said aperture by emitting a second ultrasonic pulse from said ultrasonic transducer into said structure circumferentially around said aperture and detecting a second ultrasonic echo profile from said structure; and
    providing an indication if said second echo profile deviates from said first echo profile.

17. The method of claim 16 wherein said providing an indication if said second ultrasonic echo profile deviates from said first ultrasonic echo profile comprises illuminating a light.

18. The method of claim 16 further comprising providing a second indication if said second ultrasonic echo profile does not deviate from said first ultrasonic echo profile.

19. The method of claim 18 wherein said providing an indication if said second ultrasonic echo profile deviates from said first ultrasonic echo profile comprises illuminating a first light having a first color and wherein said providing a second indication if said second ultrasonic echo profile does not deviate from said first ultrasonic echo profile comprises illuminating a second light having a second color different from said first color.

20. The method of claim 16 wherein said providing a structure comprises providing a laminated composite structure.

21. An ultrasonic aperture scanning system, comprising:
a transducer insert comprising:
   a generally elongated index portion;
   an insert plug extending from said index portion in a generally perpendicular relationship with respect to said index portion, the insert plug having a first plug section and a second plug section divided by a selectively varied plug space;
   a transducer opening provided in said index portion generally adjacent to said insert plug; and
   an ultrasonic transducer seated in said transducer opening and adapted to transmit an outgoing pulse and receive an echo signal along a path immediately adjacent and parallel to said insert plug; and
an indicator unit comprising:
   an indicator unit housing;
   a processor provided in said indicator unit housing;
   a generally elongated, flexible connecting cable connecting said processor and said ultrasonic transducer;
   a damage indicator comprising a red light carried by said indicator unit housing and interfacing with said processor; and
   a no damage indicator comprising a green light carried by said indicator unit housing and interfacing with said processor.

22. An ultrasonic aperture scanning method, comprising:
providing a structure having first and second surfaces and an aperture extending between said first and second surfaces;
providing a transducer insert having an index portion, an insert plug extending from said index portion, a transducer opening provided in said index portion generally adjacent to said insert plug and an ultrasonic transducer seated in said transducer opening, the insert plug having a first plug section and a second plug section divided by a selectively varied plug space;
extending said insert plug of said transducer insert into said aperture;
emitting a first ultrasonic pulse from said ultrasonic transducer into said structure along a path immediately adjacent and parallel to said insert plug at a reference point adjacent to said aperture;
detecting a first ultrasonic echo profile reflected from said structure along a path immediately adjacent and parallel to said insert plug;
memorizing said first ultrasonic echo profile as a reference signal;
conducting a circumferential scan into said structure around said aperture by emitting a second ultrasonic pulse from said ultrasonic transducer into said structure circumferentially around said aperture and detecting a second ultrasonic echo profile reflected from said structure;
illuminating a red light if said second echo profile deviates from said first echo profile; and
illuminating a green light if said second echo profile does not deviate from said echo profile.

* * * * *